(12) United States Patent
Hsu et al.

(10) Patent No.: US 7,244,447 B2
(45) Date of Patent: Jul. 17, 2007

(54) TRANSDERMAL ADMINISTRATION OF NONSTEROIDAL ANTI-INFLAMMATORY DRUGS USING HYDROXIDE-RELEASING AGENTS AS PERMEATION ENHANCERS

(75) Inventors: Tsung-Min Hsu, San Diego, CA (US); Eric C. Luo, Plano, TX (US)

(73) Assignee: Dermatrends, Inc., Minneapolis, MN (US)

( * ) Notice: Subject to any disclaimer, the term of this patent is extended or adjusted under 35 U.S.C. 154(b) by 289 days.

(21) Appl. No.: 10/631,539

(22) Filed: Jul. 30, 2003

(65) Prior Publication Data
US 2004/0022837 A1    Feb. 5, 2004

Related U.S. Application Data

(60) Division of application No. 09/737,830, filed on Dec. 14, 2000, now Pat. No. 6,645,520, which is a continuation-in-part of application No. 09/569,889, filed on May 11, 2000, now abandoned, which is a continuation-in-part of application No. 09/465,098, filed on Dec. 16, 1999, now abandoned.

(51) Int. Cl.
*A61F 13/00* (2006.01)
*A61L 15/00* (2006.01)

(52) U.S. Cl. ............ 424/449; 424/448; 424/443; 424/445; 424/447; 514/944; 514/946; 514/947

(58) Field of Classification Search ............ 424/449, 424/443, 445, 447, 448; 514/946, 947, 944
See application file for complete search history.

(56) References Cited

U.S. PATENT DOCUMENTS

| | | | |
|---|---|---|---|
| 4,756,710 A | * | 7/1988 | Bondi et al. ............ 424/449 |
| 4,789,547 A | | 12/1988 | Song et al. |
| 5,028,431 A | * | 7/1991 | Franz et al. ............ 424/449 |
| 5,071,657 A | | 12/1991 | Oloff et al. |
| 5,318,960 A | * | 6/1994 | Toppo ............ 514/159 |
| 5,462,744 A | | 10/1995 | Gupte et al. |
| 5,527,832 A | | 6/1996 | Chi et al. |
| 5,534,496 A | | 7/1996 | Lee et al. |

(Continued)

FOREIGN PATENT DOCUMENTS

| | | | |
|---|---|---|---|
| EP | | 0276561 | 8/1988 |
| EP | | 0709088 | 5/1996 |
| FR | | 2692145 | 12/1993 |
| JP | | 61165325 A | * 7/1986 |
| JP | | 62223118 A | * 10/1987 |
| JP | | 2180835 | 7/1990 |
| WO | WO 94/21271 | | 9/1994 |
| WO | WO 99/49844 | | 10/1999 |

OTHER PUBLICATIONS

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712-718.

*Primary Examiner*—Isis Ghali
(74) *Attorney, Agent, or Firm*—Fredrikson & Byron, P.A.

(57) ABSTRACT

A method is provided for increasing the permeability of skin or mucosal tissue to transdermally administered nonsteroidal anti-inflammatory drugs (NSAIDs). The method involves use of a specified amount of a hydroxide-releasing agent, the amount optimized to increase the flux of the NSAID through a body surface while minimizing the likelihood of skin damage, irritation or sensitization. Formulations and drug delivery systems for co-administering a hydroxide-releasing agent with an NSAID are provided as well.

44 Claims, 4 Drawing Sheets

U.S. PATENT DOCUMENTS

| | | |
|---|---|---|
| 5,573,778 A | 11/1996 | Therriault et al. |
| 5,830,497 A | 11/1998 | Yamanaka et al. |
| 5,847,003 A | 12/1998 | Ptchelintsev et al. |
| 5,879,690 A | 3/1999 | Perricone |
| 5,939,094 A | 8/1999 | Durif et al. |
| 5,962,018 A | 10/1999 | Curtis et al. |
| 5,976,566 A | 11/1999 | Samour et al. |
| 5,985,317 A | 11/1999 | Venkateshwaran et al. |
| 5,985,860 A | 11/1999 | Toppo |
| 5,989,586 A | 11/1999 | Hsu et al. |
| 5,990,113 A | 11/1999 | Yamazaki et al. |
| 5,993,851 A | 11/1999 | Foldvari |
| 6,019,988 A | 2/2000 | Parab et al. |
| 6,019,997 A | 2/2000 | Scholz et al. |
| 6,174,546 B1 | 1/2001 | Therriault et al. |
| 6,197,331 B1 | 3/2001 | Lerner et al. |
| 6,204,268 B1 | 3/2001 | Scarborough et al. |

\* cited by examiner

TRANSDERMAL ADMINISTRATION OF NONSTEROIDAL ANTI-INFLAMMATORY DRUGS USING HYDROXIDE-RELEASING AGENTS AS PERMEATION ENHANCERS

CROSS-REFERENCE TO RELATED APPLICATIONS

This is a divisional of U.S. Ser. No. 09/737,830, filed Dec. 14, 2000 now U.S. Pat. No. 6,645,520; which is a continuation-in-part of U.S. Ser. No. 09/569,889, filed May 11, 2000 now abandoned; which is a continuation-in part of U.S. Ser. No. 09/465,098, filed Dec. 16, 1999 now abandoned; the disclosures of which are incorporated by reference.

TECHNICAL FIELD

This invention relates generally to transdermal administration of pharmacologically active agents, and more particularly relates to methods and compositions for administering nonsteroidal anti-inflammatory drugs (NSAIDs) transdermally.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and a high degree of control over blood concentrations of any particular drug is made possible. Other inherent inconveniences—e.g., gastrointestinal irritation and the like—are reduced or eliminated as well. This latter advantage is particularly important with drugs that are known to be quite problematic with respect to gastrointestinal side effects. Oral administration of nonsteroidal anti inflammatory drugs, or "NSAIDs," is well known to result in mild to serious gastrointestinal side effects in a significant fraction of patients receiving the medication.

However, skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration.

With many drugs, the rate of permeation through the skin is extremely low. For example, as pointed out in U.S. Pat. No. 5,527,832 to Chi et al., the low percutaneous absorption of typical nonsteroidal anti-inflammatory drugs, i.e., propionic acid derivatives such as ketoprofen, ibuprofen, flurbiprofen, naproxen, and the like, is insufficient to allow transdermal delivery of these drugs at therapeutically effective rates. Consequently, a means for enhancing the permeability of the skin is desired to effect transport of an NSAID into and through intact skin.

In order to increase the rate at which a drug penetrates through the skin, various approaches have been followed, each of which involves the use of either a chemical penetration enhancer or a physical penetration enhancer. Physical enhancement of skin permeation include, for example, electrophoretic techniques such as iontophoresis. The use of ultrasound (or "phonophoresis") as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Various compounds for enhancing the permeability of skin are known in the art and described in the pertinent texts and literature. Compounds that have been used to enhance skin permeability include: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; organic acids, particularly salicylic acid and salicylates, citric acid and succinic acid; and certain peptides, e.g., peptides having Pro-Leu at the N-terminus and followed by a protective group (see U.S. Pat. No. 5,534,496). *Percutaneous Penetration Enhancers*, eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a pharmacologically active agent, particularly an NSAID, permeates through the skin, do not result in skin damage, irritation, sensitization, or the like. In particular, there is a need for chemical permeation enhancers that enable the effective transdermal administration of NSAIDs, "effective" administration meaning that the flux of drug through the skin is such that therapeutically effective blood levels are achieved. It has now been discovered that hydroxide-releasing agents are highly effective permeation enhancers, even when used without co-enhancers, and provide all of the aforementioned advantages relative to known permeation enhancers. Furthermore, in contrast to conventional enhancers, transdermal administration of drugs with hydroxide-releasing agents as permeation enhancers, employed at the appropriate levels, does not result in systemic toxicity.

SUMMARY OF THE INVENTION

It is thus a primary object of the invention to address the above-described need in the art by providing a method for transdermally administering a nonsteroidal anti-inflammatory drug.

It is another object of the invention to provide such a method wherein a hydroxide-releasing agent is employed as a permeation enhancer to increase the flux of the NSAID through a patient's skin or mucosal tissue.

It is still another object of the invention to provide such a method wherein the amount of hydroxide-releasing agent employed is optimized to enhance permeation while minimizing or eliminating the possibility of skin damage, irritation or sensitization.

It is an additional object of the invention to provide formulations and drug delivery systems for carrying out the aforementioned methods.

Additional objects, advantages and novel features of the invention will be set forth in part in the description that follows, and in part will become apparent to those skilled in the art upon examination of the following, or may be learned by practice of the invention.

In one aspect of the invention, then, a method is provided for increasing the rate at which a nonsteroidal anti-inflammatory drug permeates through the body surface of a patient. The method involves administering the nonsteroidal anti-inflammatory drug to a predetermined area of the patient's body surface in combination with a hydroxide-releasing agent in a predetermined amount effective to enhance the flux of the drug through the body surface without causing damage thereto. The predetermined amount of the hydroxide-releasing enhancer is preferably an amount effective to provide a pH at the body surface in the range of about 8.0 to 13, preferably about 8.0 to 11.5, more preferably about 8.5 to 11.5, during drug administration. If a skin patch is used, this is the preferred pH at the interface between the basal surface of the patch (i.e., the skin-contacting or mucosa-contacting surface of the patch) and the body surface. The optimal amount (or concentration) of any one hydroxide-releasing agent will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, more preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, e.g., treated with a dilute solution of the hydroxide-releasing agent prior to transdermal drug administration. Such a solution will generally be comprised of a protic solvent (e.g., water or alcohol) and have a pH in the range of about 8.0 to 13, preferably about 8.0 to 11.5, more preferably about 8.5 to 11.5.

In a related aspect of the invention, a composition of matter is provided for delivering a nonsteroidal anti-inflammatory drug through a body surface using a hydroxide-releasing agent as a permeation enhancer. Generally, the formulation comprises (a) a therapeutically effective amount of a drug, (b) a hydroxide-releasing agent in an amount effective to enhance the flux of the drug through the body surface without causing damage thereto, and (c) a pharmaceutically acceptable carrier suitable for topical or transdermal drug administration. The composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. In either case, it is preferred although not essential that water be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive overlayer.

In another aspect of the invention, a drug delivery system is provided for the topical or transdermal administration of a nonsteroidal anti-inflammatory drug using a hydroxide-releasing agent as a permeation enhancer. The system will generally comprise: at least one drug reservoir containing the drug and the hydroxide-releasing agent in an amount effective to enhance the flux of the drug through the body surface without causing damage thereto; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"-type structure wherein the drug and hydroxide-releasing agent are present in the pouch as a liquid or semi-solid formulation.

DETAILED DESCRIPTION OF THE INVENTION

Definitions and Overview

Figure 1:
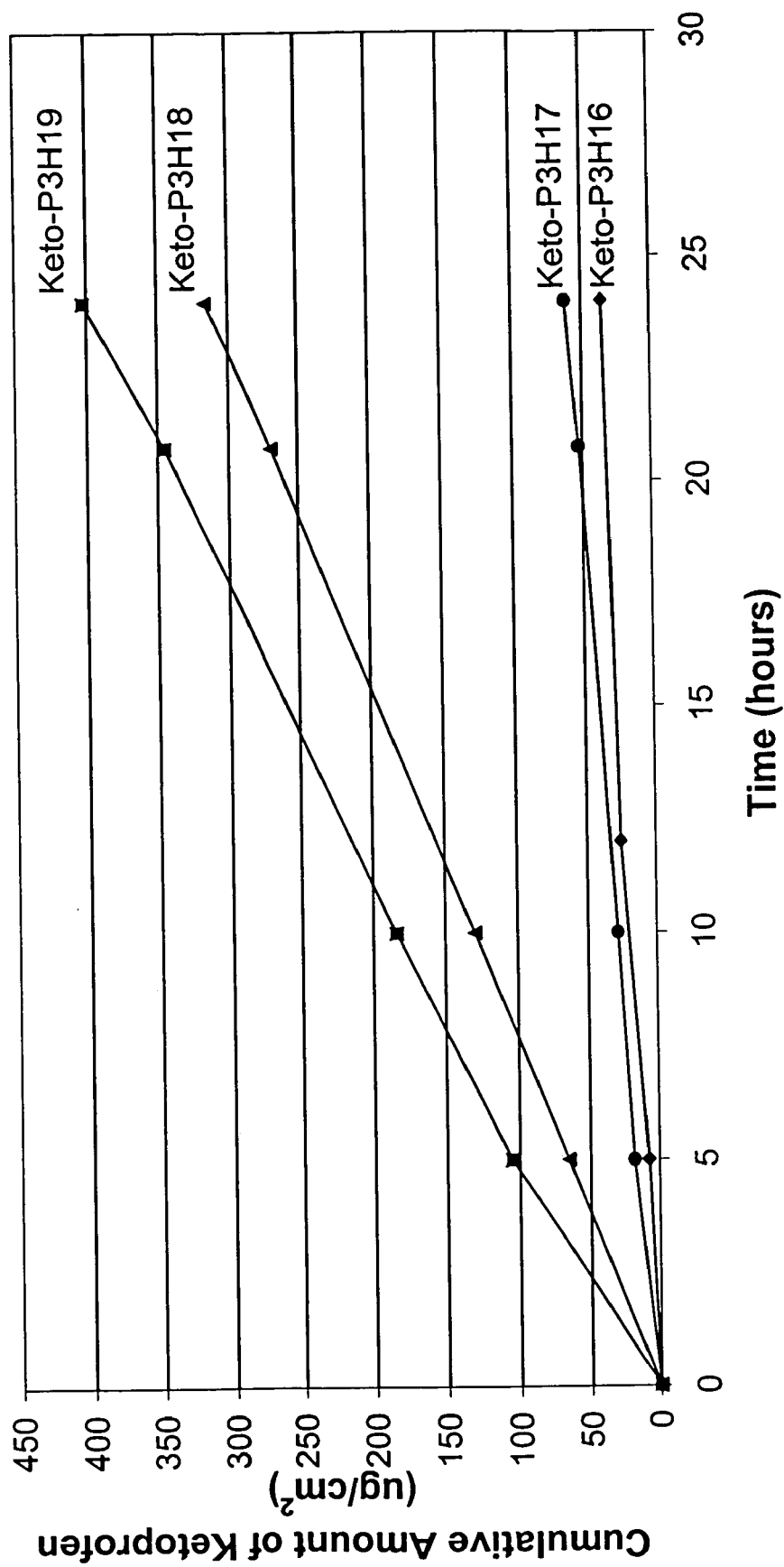
FIG. 1 is a graph illustrating the cumulative amount of ketoprofen from a matrix patch as described in Example 1.

Before describing the present invention in detail, it is to be understood that this invention is not limited to specific drug delivery systems, device structures, enhancers or carriers, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a nonsteroidal anti-inflammatory drug" includes a mixture of two or more such drugs, reference to "a hydroxide-releasing agent" includes mixtures of two or more hydroxide-releasing agents, and the like.

In describing and claiming the present invention, the following terminology will be used in accordance with the definitions set out below.

The terms "drug" or "pharmacologically active agent" or "active agent" as used herein refer to a compound or composition of matter which, when administered to an organism (human or animal) induces a desired pharmacologic and/or physiologic effect by local and/or systemic action. The active agents herein are nonsteroidal anti-inflammatory agents and pharmacologically acceptable salts, esters, amides, derivatives or prodrugs thereof.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be on that is acted upon chemically in an aqueous environment to generate hydroxide ions (e.g., a metal carbonate).

By "therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug of a pharmacologically active agent to the skin or mucosa, as in, for example, the treatment of various skin disorders. Topical drug administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which a drug-enhancer formulation is delivered, is intended a defined area of intact unbroken living skin or mucosal tissue. That area will usually be in the range of about 5 $cm^2$ to about 200 $cm^2$, more usually in the range of about 5 $cm^2$ to about 100 $cm^2$, preferably in the range of about 20 $cm^2$ to about 60 $cm^2$. However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art and as employed in the Examples herein.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which are nontoxic and does not interact with other components of the composition in a deleterious manner.

The term "aqueous" refers to a formulation or drug delivery system that contains water or that becomes water-containing following application to the skin or mucosal tissue.

Accordingly, the invention pertains to a method, composition and drug delivery system for increasing the rate at which a nonsteroidal anti-inflammatory drug permeates through the body surface of a patient, wherein the method involves administering the drug to a predetermined area of the patient's body surface in combination with a hydroxide-releasing agent in an amount effective to enhance the flux of the drug through the body surface without causing damage thereto.

The Hydroxide-Releasing Agent

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium carbonate, sodium bicarbonate, sodium phosphate (tribasic), sodium phosphate (dibasic), sodium borate, sodium metaborate, potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of the nonsteroidal anti-inflammatory drug through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of the formulation or the drug composition contained within a delivery system will be in the range of approximately 8.0 to 13, preferably 8.0 to 11.5, more preferably 8.5 to 11.5.

For inorganic hydroxides, the amount of hydroxide-releasing agent will typically represent about 0.5 wt % to 4.0 wt %, preferably about 0.5 wt % to 3.0 wt %, more preferably about 0.75 wt % to 2.0 wt % and optimally about 1.0 wt %, of a topically applied formulation or of a drug reservoir or a drug delivery system, or "patch." The aforementioned amount applies to formulations and patches in which the drug is (1) an uncharged molecule, either an uncharged, nonionizable compound or a basic drug in nonionized, free base form, or (2) a basic addition salt of an acid drug, and where (3) there are no additional species in the formulation or patch that could react with or be neutralized by the inorganic hydroxide. For formulations and patches in which the active agent is an acid addition salt of a basic drug or is a drug that reacts with the hydroxide-releasing agent, e.g., an acidic drug in nonionized, free acid form, and/or wherein there are additional species in the formulations or systems that can be neutralized by or react with the hydroxide-releasing agent (i.e., acidic inactive ingredients), the amount of inorganic hydroxide will be the total of (1) the amount necessary to neutralize or react with the drug and/or other base-neutralizable species, plus (2) about 0.5 wt % to 4.0 wt %, preferably about 0.5 wt % to 3.0 wt %, more preferably about 0.75 wt % to 2.0 wt % and optimally about 1.0 wt %, of the formulation or drug reservoir. That is, for acid addition salts of basic drugs and nonionized acidic drugs, the inorganic hydroxide should be present in an amount just sufficient to neutralize the drug, plus an additional amount (i.e., about 0.5 wt % to 4.0 wt %, preferably about 0.5 wt % to 3.0 wt %, more preferably about 0.75 wt % to 2.0 wt % and optimally about 1.0 wt %) to enhance the flux of the drug through the skin or mucosal tissue. (By "neutralization" of a free acid is meant conversion of the free acid, via ionization, to a salt.) For patches, the aforementioned percentages are given relative to the total dry weight of the formulation components and the adhesive, gel or liquid reservoir.

For other hydroxide-releasing agents such as inorganic oxides and metal salts of weak acids, the amount of hydroxide-releasing agent in the formulation or drug delivery system may be substantially higher, as high as about 20 wt %, in some cases as high as about 25 wt % or higher, but will generally be in the range of about 2 wt % to about 20 wt %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation or drug delivery system should in all cases be effective to provide a pH at the skin surface in the range of about 8.0 to 13, preferably in the range of about 8.0 to 11.5, more preferably in the range of about 8.5 to 11.5, during application to reach the desired pH at the body surface. This in turn ensures that the degree of enhancement is optimized while the possibility of damage to the body surface is eliminated or at least substantially minimized.

The Active Agent(s)

Suitable nonsteroidal anti inflammatory agents that may be used in the formulations of the present invention include, but are not limited to: propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing. Preferred NSAIDs are ibuprofen, diclofenac sodium, ketoprofen, ketorolac and piroxicam.

Pharmaceutically acceptable analogs of such NSAIDs are suitable as well, including salts, esters, amides, prodrugs or other derivatives.

The NSAID or NSAIDs may be co-administered with one or more additional active agents, e.g.: antihistaminic agents such as diphenhydramine and chlorpheniramine (particularly diphenhydramine hydrochloride and chlorpheniramine maleate); corticosteroids, including lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21diacetate, hydrocortisone-17-acetate-21-butyrate, hydrocortisone-17,21-dibutyrate, etc.), alclometasone, dexamethasone, flumethasone, prednisolone, and methylprednisolone, as well as higher potency corticosteroids such as clobetasol propionate, betamethasone benzoate, betamethasone diproprionate, diflorasone diacetate, fluocinonide, mometasone furoate, triamcinolone acetonide, and the like; local anesthetic agents such as phenol, benzocaine, lidocaine, prilocaine and dibucaine; topical analgesics such as glycol salicylate, methyl salicylate, 1-menthol, d,1-camphor and capsaicin; and antibiotics. Suitable antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin itself (6,8-dideoxy-6-[[(1-methyl-4propyl-2-pyrrolidinyl)-carbonyl]amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]amino]-1-thio-L-threo-α-D-galacto-octopyranoside), related compounds as described, for example, in U.S. Pat. Nos. 3,475, 407, 3,509,127, 3,544,551 and 3,513,155, and pharmacologically acceptable salts and esters thereof. Exemplary antibiotics of the tetracycline family include tetracycline itself (4-(dimethylamino)1,4,4α,5,5α,6,11,12α-octahydro-3,6,12,12α-pentahydroxy-6-methyl-1,11-dioxo-2naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfanethazine, sulfamethizole, sulfamethoxazole, and pharmacologically acceptable salts and esters thereof, e.g., sulfacetamide sodium.

To administer any one of the active agents in salt form, suitable pharmaceutically acceptable salts can be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992). Acid addition salts are prepared from an active agent in the free base form (e.g., compounds having a neutral —NH$_2$ group) using conventional means, involving reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Preparation of esters involves functionalization of carboxyl groups that may be present, as will be appreciated by those skilled in the arts of pharmaceutical chemistry and drug delivery. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

For those active agents that are chiral in nature and can thus be in enantiomerically pure form or in a racemic mixture, the drug may be incorporated into the present dosage units either as the racemate or in enantiomerically pure form.

Formulations

The method of delivery of the NSAID may vary, but necessarily involves application of a formulation or drug delivery system containing the drug and a hydroxide-releasing agent to a predetermined area of the skin or other tissue for a period of time sufficient to provide the desired local or systemic effect. The method may involve direct application of the composition as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive overlayer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy,* 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the hydroxide-releasing agent, although in a preferred embodiment the hydroxide-releasing agent is administered without any other permeation enhancers. Any other enhancers should, like the hydroxide-releasing agent itself, minimize the possibility of skin damage, irritation, and systemic toxicity. Examples of suitable secondary enhancers (or "co-enhancers") include, but are not limited to: ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred. As noted earlier herein, *Percutaneous Penetration Enhancers*, eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the drug, the enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt %, more typically not more than about 5 wt %, of the formulations.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. The formulations will typically contain on the order of about 0.5 wt % to 50 wt % active agent, preferably about 0.5 wt % to 5 wt % active agent, optimally about 5 wt % to 20 wt % active agent.

Drug Delivery Systems

An alternative and preferred method involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene(polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of drug to be delivered and the flux of the drug through the body surface. Larger patches will be necessary to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such an adhesive overlayer, the delivery system remains in place for the required period of time.

Other types and configurations of transdermal drug delivery systems may also be used in conjunction with the method of the present invention, i.e., the use of a hydroxide-releasing agent as a permeation enhancer, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the topically applied formulations of the invention, the composition containing drug and hydroxide-releasing agent within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Utility

The amount of drug present in the formulations and drug delivery systems of the invention and required to achieve an effective therapeutic result depends on many factors, such as the particular NSAID selected, the minimum necessary dosage of the drug for the particular indication being treated, the solubility and permeability of the carrier and adhesive layer, and the period of time for which the device will be affixed to the skin or other body surface. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

The transdermal delivery formulations and systems of the invention are used to treat an individual with an NSAID-responsive condition or disorder. Typically, the formulations are employed as anti-inflammatory and/or analgesic compositions, and may be used to treat individuals suffering from rheumatic or arthritic disorders, including, for example: rheumatoid arthritis (RA), degenerative joint disease (also known as DJD and "osteoarthritis"); juvenile rheumatoid arthritis (JRA); psoriatic arthritis; gouty arthritis; ankylosing spondylitis; and lupus erythematoses such as systemic lupus erythematosus and discoid lupus erythematosus.

Other potential uses for the formulation of the present invention include, but are not limited to, treating fever (via the anti-pyretic property of NSAIDs) or myocardial infarction (MI), transient ischemic attacks, and acute superficial thrombophlebitis (via inhibition of platelet aggregation). Further non-limiting uses for NSAIDs include either single or adjuvant therapy for ankylosing spondylitis, bursitis, cancer-related pain, dysmenorrhea, gout, headaches, muscular pain, tendonitis, and pain associated with medical procedures such as dental, gynecological, oral, orthopedic, post-partum and urological procedures.

As noted above, the amount of active compound administered will depend on a number of factors and will vary from subject to subject and depend on the particular active agent administered, the particular disorder or condition, the severity of the symptoms, the subject's age, weight and general condition, and the judgment of the prescribing physician. Other factors specific to transdermal drug delivery include the solubility and permeability of the carrier and the adhesive layer in a drug delivery system, if one is used, and the period of time for which such a device will be affixed to the skin or other body surface. Generally, however, and by way of example, a daily dosage of ketorolac using the present formulations and systems will be in the range of approximately 10 mg to 40 mg, a daily dosage of piroxicam using the present formulations and systems will be in the range of approximately 10 mg to 40 mg, and a daily dosage of ibuprofen using the present formulations and systems will be in the range of approximately 200 mg/day to 1600 mg/day.

The invention accordingly provides a novel and highly effective means for increasing the flux of a nonsteroidal anti-inflammatory drug through the body surface (skin or mucosal tissue) of a human or animal. The hydroxide-releasing agents discussed herein, employed in specific amounts relative to a formulation or drug reservoir, may be used as permeation enhancers with a variety of nonsteroidal anti-inflammatory drugs, including, but not limited to, ibuprofen, diclofenac sodium, ketoprofen, ketorolac and piroxicam. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

EXAMPLE 1

An in vitro skin permeation study was conducted using four ketoprofen transdermal systems. The formulations used to prepare these systems are listed in Table 1, which includes weight and weight percent of each component of the formulations. The weight of sodium hydroxide was 0 g, 0.19 g, 0.215 g, and 0.225 g for formulation #Keto-P3H16, -P3H17, -P3H18, and -P3H19, respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into discs with a diameter of 11/16 inch. The theoretical percent weight for each ingredient after drying (calculated assuming all volatile ingredients were completely removed during drying) is set forth in Table 2.

The in vitro permeation of ketoprofen through human cadaver skin from these discs was performed using Franz diffusion cells with a diffusion area of 1 cm². Human cadaver skin was cut to a proper size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Five diffusion cells were used for each formulation.

Normal saline was used as the receiver solution. The volume of receiver solution was 8 ml. The entire receiver solution was collected and replaced with fresh saline at each time point. The receiver solution collected was analyzed by HPLC to determine the concentration of ketoprofen. The cumulative amount of ketoprofen that permeated across the human cadaver skin was calculated using the measured ketoprofen concentrations in the receiver solutions, which were plotted versus time and shown in FIG. 1.

Since ketoprofen is a free acid, it reacts with NaOH. The concentration of NaOH in the system after the reaction is completed depends on the amount of ketoprofen added. The remaining NaOH concentration after the reaction is completed is defined as "excess NaOH concentration," which is calculated by the following equation.

$$[NaOH_{excess}] = [NaOH_{total}] - [NaOH_{needed\ for\ neutralization}]$$

The excess NaOH concentrations for three ketoprofen systems, #Keto-P3H16, -P3H17, -P3H18, and -P3H19, were calculated and are set forth in Table 3.

The pH of each patch was measured using the following procedures. A 2.5 cm² circular patch was punched out. Ten ml purified water was pipetted into a glass vial, and a stir bar was added; the liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. The stir bar was removed from the vial and the pH of the solution determined using a calibrated pH meter. The results are set forth in Table 3.

TABLE 1

Weight and Weight Percent of Each Component (Based on Total Solution Weight) for Four Ketoprofen Transdermal Systems

|  | Keto-P3H16 | Keto-P3H17 | Keto-P3H18 | Keto-P3H19 |
|---|---|---|---|---|
| Ketoprofen | 1.2 g (16.7%) | 1.2 g (15.8%) | 1.2 g (15.7%) | 1.2 g (15.7%) |
| NaOH | 0 | 0.19 g (2.5%) | 0.215 g (2.8%) | 0.225 g (2.9%) |

TABLE 1-continued

Weight and Weight Percent of Each Component (Based on Total Solution Weight) for Four Ketoprofen Transdermal Systems

|  | Keto-P3H16 | Keto-P3H17 | Keto-P3H18 | Keto-P3H19 |
|---|---|---|---|---|
| DI water | 0 | 0.19 g (2.5%) | 0.215 g (2.8%) | 0.225 g (2.9%) |
| PIB adhesive (30% solid) | 4 g (55.6%) | 4 g (52.8%) | 4 g (52.4%) | 4 g (52.3%) |
| Methylal | 2 g (27.8%) | 2 g (26.4%) | 2 g (26.2%) | 2 g (26.1%) |

TABLE 2

Weight and Theoretical Weight Percent of Each Component in the Dried Film for Four Ketoprofen Transdermal Systems

|  | Keto-P3H16 | Keto-P3H17 | Keto-P3H18 | Keto-P3H19 |
|---|---|---|---|---|
| Ketoprofen | 1.2 g (50%) | 1.2 g (45.9%) | 1.2 g (45.9%) | 1.2 g (45.7%) |
| NaOH | 0 | 0.19 g (7.3%) | 0.215 g (8.2%) | 0.225 g (8.6%) |
| PIB adhesive | 1.2 g (50%) | 1.2 g (46.3%) | 1.2 g (45.9%) | 1.2 g (45.7%) |

TABLE 3

Excess NaOH Concentration and pH of Four Ketoprofen Transdermal Systems

|  | Keto-P3H16 | Keto-P3H17 | Keto-P3H18 | Keto-P3H19 |
|---|---|---|---|---|
| Excess NaOH Concentration |  | 0.05% | 1.00% | 1.38% |
| pH | 3.68 | 8.60 | 10.10 | 10.57 |

Even though patch #Keto-P3H17 contained 7.3% NaOH (Table 2), the cumulative amount of ketoprofen that permeated across the human cadaver skin at 24 hours (61.7 µg/cm², FIG. 1) was only slightly higher than that from the formulation without NaOH (Keto-P3H16, 35.2 µg/cm²). This may be due to the consumption of NaOH by the reaction between NaOH and ketoprofen, which reduced the NaOH concentration to only 0.05% as the excess NaOH concentration (Table 3). This result indicated that the permeation of ketoprofen could be enhanced with an excess NaOH concentration as low as 0.05%.

The cumulative amount of ketoprofen that permeated across human cadaver skin at 24 hours increased from 61.7 µg/cm² to 402.7 µg/cm² when the calculated excess NaOH concentration in the dried patch was increased from 0.05% to 1.38%. The cumulative amount of ketoprofen that permeated across human cadaver skin at 24 hours from the formulation with an excess NaOH concentration of 1.00% (Keto-P3H18, 315.8 µg/cm²) is about 5 times higher than that from the formulation with an excess NaOH concentration of 0.05% (Keto-P3H17, 61.7 µg/cm²).

The pH of the ketoprofen patch increased from 8.60 to 10.57 when the calculated excess NaOH concentration in the dried patch was increased from 0.05% to 1.38%.

EXAMPLE 2

A human skin irritation study was performed using seven transdermal systems, which are listed below.

Patch #Keto-IT1 (containing no ketoprofen, no NaOH)
Patch #Keto-IT2 (containing ketoprofen, no NaOH)
Patch #Keto-IT7
Patch #Keto-IT8
Patch #Keto-IT9
Patch #Keto-IT10
Patch containing petrolatum The patch containing petrolatum was used as a control, which was an occlusive chamber (Hilltop, Cincinnati, Ohio) containing petrolatum held in place with paper tape. The following procedures were used to prepare the systems with the exception of the system containing petrolatum. The formulations used to prepare these systems are listed in Table 4, which include weight and weight percent of each component in the formulations. The weight of sodium hydroxide was 0.6 g, 0.65 g, 0.69 g, and 0.73 g for formulation #Keto-IT7, -IT8, -IT9 and -IT10 respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was cut into round discs with a diameter of ½ inch. The theoretical percent weight for each ingredient after drying is listed in Table 5, which was calculated assuming all the volatile ingredients were completely removed during drying.

Ten healthy human subjects were included in the skin irritation study. Each subject worn seven patches listed above on the arms for 24 hours. An adhesive film with a diameter of ⅞ inch was applied over each system on the skin except the petrolatum patch to secure the system and to make the system occlusive for 24 hours. After 24 hours, the patches were removed and the skin was scored on a 0-4 scale. The scoring scale employed is listed below. The skin was scored again at 48 hours.
  0=negative
  +=equivocal reaction (0.5)
  1=erythema
  2=erythema and induration
  3=erythema, induration and vesicles
  4=bullae A skin permeation study was performed from formulation #Keto-IT7, -IT8, -IT9 and -IT10. Franz diffusion cells with a diffusion area of 1 cm$^2$ were used in this study. Human cadaver skin was cut to a proper size and placed on a flat surface with the stratum corneum side facing up. The release liner was peeled away from the round disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

Normal saline was used as the receiver solution. The volume of receiver solution was 8 ml. The receiver solution was collected at 24 hours and analyzed by an HPLC for the concentration of ketoprofen. The amount of ketoprofen that permeated across the human cadaver skin was calculated using the measured ketoprofen concentrations in the receiver solutions, which are listed in Table 6.

The excess NaOH concentrations for four ketoprofen systems, #Keto -IT7, -IT8, -IT9 and -IT10 were calculated as the preceding examples and listed in Table 6.

The pH of the patch was determined using the procedure of Example 1, and the measured pH for each ketoprofen transdermal systems is also listed in Table 6.

TABLE 4

Weight and Weight Percent of Each Component (Based on Total Solution Weight) for Four Ketoprofen Transdermal Systems

|  | Keto-IT7 | Keto-IT8 | Keto-IT9 | Keto-IT10 |
|---|---|---|---|---|
| Ketoprofen | 2.4 g (14.0%) | 2.4 g (14.0%) | 2.4 g (13.9%) | 2.4 g (13.8%) |
| NaOH | 0.6 g (3.5%) | 0.65 g (3.8%) | 0.69 g (4.0%) | 0.73 g (4.2%) |
| DI water | 0.6 g (3.5%) | 0.65 g (3.8%) | 0.69 g (4.0%) | 0.73 g (4.2%) |
| PIB adhesive (30% solid) | 8 g (46.8%) | 8 g (46.5%) | 8 g (46.3%) | 8 g (46.1%) |
| Tetraglycol | 0.5 g (2.9%) | 0.5 g (2.9%) | 0.5 g (2.9%) | 0.5 g (2.9%) |
| Isopropylmyristate | 0.4 g (2.3%) | 0.4 g (2.3%) | 0.4 g (2.3%) | 0.4 g (2.3%) |
| Methyl salicylate | 0.6 g (3.5%) | 0.6 g (3.5%) | 0.6 g (3.5%) | 0.6 g (3.5%) |
| Methylal | 4 g (23.4%) | 4 g (23.3%) | 4 g (23.3%) | 4 g (23.0%) |

TABLE 5

Weight and Theoretical Weight Percent of Each Component in the Dried Film for Four Ketoprofen Transdermal Systems

|  | Keto-IT7 | Keto-IT8 | Keto-IT9 | Keto-IT10 |
|---|---|---|---|---|
| Ketoprofen | 2.4 g (34.8%) | 2.4 g (34.5%) | 2.4 g (34.3%) | 2.4 g (34.1%) |
| NaOH | 0.6 g (8.7%) | 0.65 g (9.4%) | 0.69 g (9.9%) | 0.73 g (10.4%) |
| PIB adhesive | 2.4 g (34.0%) | 2.4 g (34.5%) | 2.4 g (34.3%) | 2.4 g (34.1%) |
| Tetraglycol | 0.5 g (7.2%) | 0.5 g (7.2%) | 0.5 g (7.2%) | 0.5 g (7.1%) |
| Isopropylmyristate | 0.4 g (5.8%) | 0.4 g (5.8%) | 0.4 g (5.7%) | 0.4 g (5.7%) |
| Methyl salicylate | 0.6 g (8.7%) | 0.6 g (8.6%) | 0.6 g (8.6%) | 0.6 g (8.5%) |

TABLE 6

Excess NaOH Concentration, Cumulative Amount of Ketoprofen across Skin at 24 Hours and pH of Four Ketoprofen Transdermal Systems

|  | Keto-IT7 | Keto-IT8 | Keto-IT9 | Keto-IT10 |
|---|---|---|---|---|
| pH | 10.06 | 10.81 | 11.04 | 11.18 |
| Excess NaOH Concentration | 3.22% | 3.92% | 4.47% | 5.01% |
| Cumulative amount across skin at 24 hours mg/cm$^2$ | 0.17 | 0.34 | 0.54 | 1.52 |

The cumulative amount of ketoprofen that permeated across the human cadaver skin at 24 hours increased from 0.17 mg/cm$^2$ to 1.52 mg/cm$^2$ when the calculated excess NaOH concentration in the dried patch was increased from 3.22% to 5.01%. The excess NaOH concentration and the cumulative amount of ketoprofen across skin at 24 hours and the patch pH for Keto-IT8 was 0.34 mg/cm$^2$ and 10.81 respectively, which was about the same as those for Keto-P3H18 shown in Example 1 (0.32 mg/cm$^2$, pH=10.10). However, the excess NaOH concentration for Keto-IT8 (3.92%) was higher than that for Keto-P3H18 (1.00%) which may be due to the consumption of NaOH through reactions between NaOH and components other than ketoprofen in the Keto-IT8 formulation.

The irritation scores obtained indicate that irritation from this patch was insignificant.

EXAMPLE 3

An in vitro skin permeation study was conducted using four ibuprofen transdermal gels. The formulations used to prepare these gels are listed in Table 7, which includes weight and weight percent of each component in the formulations. The weight of sodium hydroxide was 0 g, 0.115 g, 0.135 g, and 0.15 g for formulation #Ibu-GH81, -GH82, -GH83, and -GH84 respectively.

The in vitro permeation of ibuprofen through human cadaver skin from these gels was performed using Franz diffusion cells with a diffusion area of 1 cm². Human cadaver skin was cut to a proper size and clamped between the donor and receiver chambers of the diffusion cell with the stratum corneum side facing the donor solution. Three diffusion cells were used for each formulation.

Figure 2:
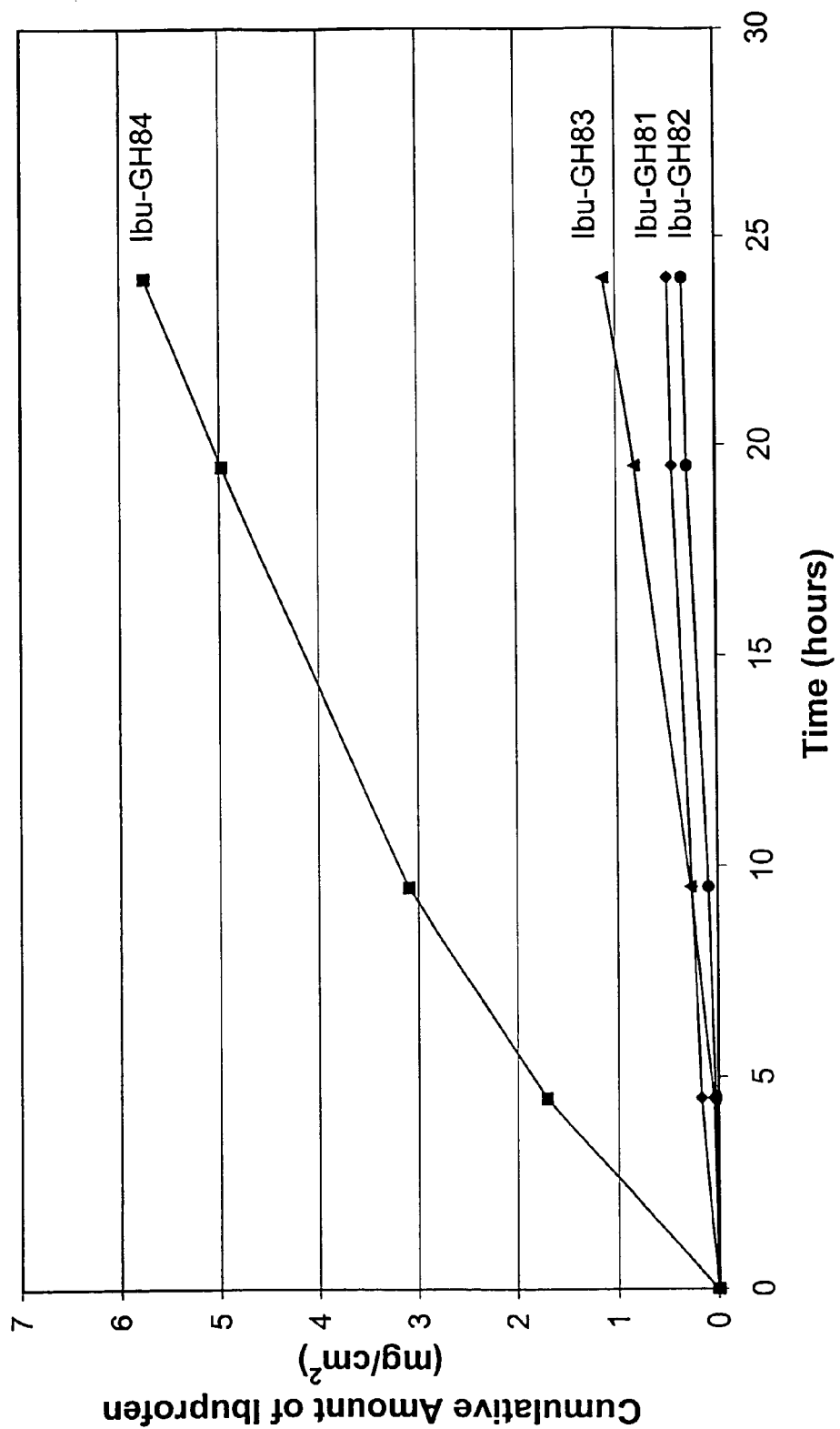
FIG. 2 is a graph illustrating the cumulative amount of ibuprofen from a gel described in Example 3.

Normal saline was used as the receiver solution. The volume of receiver solution was 8 ml. The entire receiver solution was collected and replaced with fresh saline at each time point. The receiver solution collected was analyzed by an HPLC for the concentration of ibuprofen. The cumulative amount of ibuprofen across human cadaver skin was calculated using the measured ibuprofen concentrations in the receiver solutions, which were plotted versus time and shown in FIG. 2.

The excess NaOH concentration for three ibuprofen gels, #Ibu-GH81, -GH82, GH83, and -GH84, were calculated and listed in Table 8.

The pH of each gel was determined as done previously. The measured pHs for the ibuprofen gels are listed in Table 8.

TABLE 7

Weight and Weight Percent of Each Component (Based on Total Solution Weight) for Four Ibuprofen Transdermal Gels

|  | Ibu-GH81 | Ibu-GH82 | Ibu-GH83 | Ibu-GH84 |
|---|---|---|---|---|
| Ibuprofen | 0.6 g | 0.6 g | 0.6 g | 0.6 g |
|  | (36.8%) | (32.3%) | (31.6%) | (31.1%) |
| NaOH | 0 | 0.115 g | 0.135 g | 0.15 g |
|  |  | (6.2%) | (7.1%) | (7.8%) |
| Ethanol | 0.4 g | 0.4 g | 0.4 g | 0.4 g |
|  | (24.5%) | (21.5%) | (21.1%) | (20.7%) |
| DI Water | 0.6 g | 0.715 g | 0.735 g | 0.75 g |
|  | (36.8%) | (38.4%) | (38.7%) | (38.9%) |
| HPMCP* | 0.03 g | 0.03 g | 0.03 g | 0.03 g |
|  | (1.8%) | (1.6%) | (1.6%) | (1.6%) |

*HPMCP = Hydroxypropyl methyl cellulose phthalate

TABLE 8

Excess NaOH Concentration and pH of Four Ibuprofen Transdermal Gels

|  | Ibu-GH81 | Ibu-GH82 | Ibu-GH83 | Ibu-GH84 |
|---|---|---|---|---|
| Excess NaOH Concentration |  | 0% | 0.98% | 1.74% |
| pH | 4.57 | 6.58 | 11.83 | 12.22 |

The cumulative amount of ibuprofen across human cadaver skin at 24 hours increased from 0.33 mg/cm² to 5.74 mg/cm² (FIG. 2) when the calculated excess NaOH concentration in the gel was increased from 0% to 1.74%. The cumulative amount of ibuprofen that permeated across the human cadaver skin at 24 hours from the formulation with an excess NaOH concentration of 0.98% (Ibu-GH83, 1.12 mg/cm²) is about 3 times higher than that from the formulation with an excess NaOH concentration of 0% (Ibu-GH82, 0.33 mg/cm²).

The pH of the ibuprofen patch determined using the procedures of the previous examples increased from 6.58 to 12.22 when the calculated excess NaOH concentration in the gel was increased from 0% to 1.74%. The skin irritation could be related to the pH of the gel, which depends on the excess NaOH concentration.

EXAMPLE 4

An in vitro skin permeation study was conducted using four diclofenac sodium transdermal systems. The formulations used to prepare these systems are listed in Table 9, which include weight and weight percent of each ingredient in the formulations. The weight of sodium hydroxide (NaOH) was 0 g, 0.035 g, 0.05 g, and 0.1 g for formulation #Diclo-P1O, -P11, -P12, and -P13 respectively. Each formulation was coated on a release liner and dried in an oven at 55 □C for two hours to remove water and other solvents. The dried drug-in-adhesive/release liner film was laminated to a backing film. The backing/drug-in-adhesive/release liner laminate was then cut into round discs with a diameter of ¹¹⁄₁₆ inch. The theoretical percent weight for each ingredient after drying (calculated assuming all the volatile ingredients were completely removed during drying) is listed in Table 10.

The in vitro permeation of diclofenac sodium through human cadaver skin from these discs was performed using Franz-type diffusion cells with a diffusion area of 1 cm². The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

Figure 3:
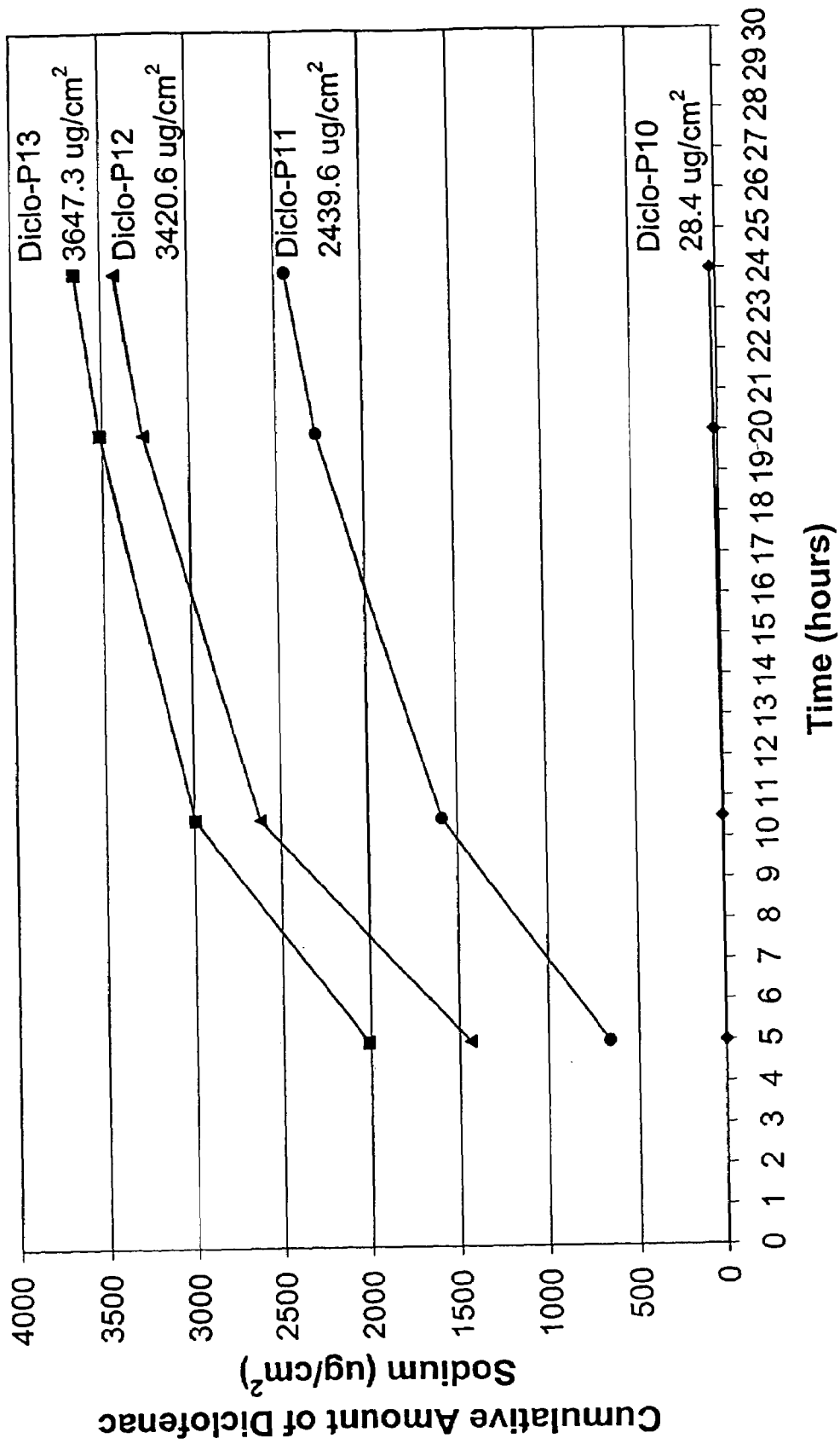
FIG. 3 is a graph illustrating the cumulative amount of diclofenac from a matrix patch as described in Example 4.

The cells were filled with 10% ethanol/90% water solution. The receiver solution was completely withdrawn and replaced with fresh ethanol/water solution at each time point. The samples taken were analyzed by an HPLC for the concentration of diclofenac sodium in the receiver solution. The cumulative amount of diclofenac sodium across human cadaver skin was calculated using the measured diclofenac sodium concentrations in the receiver solutions, which are shown in Table 11 and FIG. 3.

Since diclofenac sodium is not expected to react with NaOH, the NaOH concentration listed in Table 10 equals the excess NaOH concentration.

The pH of the patch was determined using the following procedures. A 2.5 cm² circular patch was punched out. Ten ml purified water was pipetted into a glass vial, and a stir bar was added, the liner was removed from patch and placed in the vial along with the patch. The vial was then placed on a stir plate and the water/patch/liner mixture was stirred for 5 minutes, at which point the liner was removed from the vial and discard. The vial was again placed on a stir plate and stirring continued for an additional 18 hours. After 18 hours, the stir bar was removed from vial and the pH of the solution determined using a calibrated pH meter.

The measured pHs for the diclofenac sodium transdermal systems are listed in Table 12.

TABLE 9

Weight and Weight Percent of Each Component (Based on Total Solution Weight) for Four Diclofenac Sodium Transdermal Systems

|  | Diclo-P10 | Diclo-P11 | Diclo-P12 | Diclo-P13 |
|---|---|---|---|---|
| Diclofenac sodium | 0.6 g (9.2%) | 0.6 g (9.1%) | 0.6 g (9.0%) | 0.6 g (9.0%) |
| Propylene glycol | 0.9 g (13.9%) | 0.9 g (13.7%) | 0.9 g (13.6%) | 0.9 g (13.4%) |
| NaOH | 0 | 0.035 g (0.5%) | 0.05 g (0.8%) | 0.1 g (1.5%) |
| PIB adhesive (30% solid) | 4 g (61.5%) | 4 g (60.9%) | 4 g (60.6%) | 4 g (59.7%) |
| Heptane | 1 g (15.4%) | 1 g (15.2%) | 1 g (15.2%) | 1 g (14.9%) |
| DI water | 0 | 0.035 g (0.5%) | 0.05 g (0.8%) | 0.1 g (1.5%) |

TABLE 10

Weight and Theoretical Weight Percent of Component in the Dried Film for Four Diclofenac Sodium Transdermal Systems

|  | Diclo-P10 | Diclo-P11 | Diclo-P12 | Diclo-P13 |
|---|---|---|---|---|
| Diclofenac sodium | 0.6 g (22.2%) | 0.6 g (21.9%) | 0.6 g (21.8%) | 0.6 g (21.4%) |
| Propylene glycol | 0.9 g (33.3%) | 0.9 g (32.9%) | 0.9 g (32.7%) | 0.9 g (32.1%) |
| NaOH | 0 | 0.035 g (1.3%) | 0.05 g (1.8%) | 0.1 g (3.6%) |
| PIB adhesive (30% solid) | 1.2 g (44.4%) | 1.2 g (43.9%) | 1.2 g (43.6%) | 1.2 g (42.9%) |

TABLE 11

Cumulative Amount of PPA-HCl across human cadaver skin for Diclofenac Sodium Transdermal Systems ($\mu g/cm^2$)

|  | Diclo-P10 | Diclo-P11 | Diclo-P12 | Diclo-P13 |
|---|---|---|---|---|
| 5 hours | 0.5 | 659.0 | 1437.8 | 2010.5 |
| 10.5 hours | 4.7 | 1587.6 | 2619.3 | 2992.9 |
| 20 hours | 18.8 | 2273.7 | 3263.0 | 3513.1 |
| 24 hours | 28.4 | 2439.6 | 3420.6 | 3647.3 |

TABLE 12

Excess NaOH Concentration and pH of Four Diclofenac Sodium Transdermal Systems

|  | Diclo-P10 | Diclo-P11 | Diclo-P12 | Diclo-P13 |
|---|---|---|---|---|
| Excess NaOH Concentration (wt %) | 0 | 1.3 | 1.8 | 3.6 |
| pH | 7.17 | 10.59 | 10.72 | 11.28 |

The cumulative amount of diclofenac sodium across human cadaver skin at 24 hours increased from 28.4 $\mu g/cm^2$ to 3647.3 $\mu g/cm^2$ when the calculated excess NaOH concentration in the dried patch was increased from 0% to 3.6%. The cumulative amount of diclofenac sodium across human cadaver skin at 24 hours from the system containing 0% NaOH (Diclo-P11) was 2439.6 $\mu g/cm^2$, which was about 85 times higher than that from the formulation without NaOH (28.4 $\mu g/cm^2$, #Diclo-P10).

The pH of the diclofenac sodium patch measured using the procedures listed above increased from 7.17 to 11.28 when the calculated excess NaOH concentration in the dried patch was increased from 0% to 3.6%.

EXAMPLE 5

An in-vitro skin permeation study was conducted using four diclofenac sodium transdermal gels. The formulations used to prepare these gels are listed in Table 53, which include weight and weight percent of each ingredient in the formulations. The weight of sodium hydroxide (NaOH) was 0 g, 0.02 g, 0.03 g, and 0.05 g for formulation #Diclo-DG25, -DG27, -DG28, and -DG29 respectively.

The in-vitro permeation of diclofenac sodium through human cadaver skin from these gels was performed using Franz-type diffusion cells with a diffusion area of 1 $cm^2$. Human cadaver skin was cut to desired size and clamped between the donor and receiver chambers of the diffusion cell with the stratum corneum side facing the donor solution. Three diffusion cells were used for each formulation.

Figure 4:
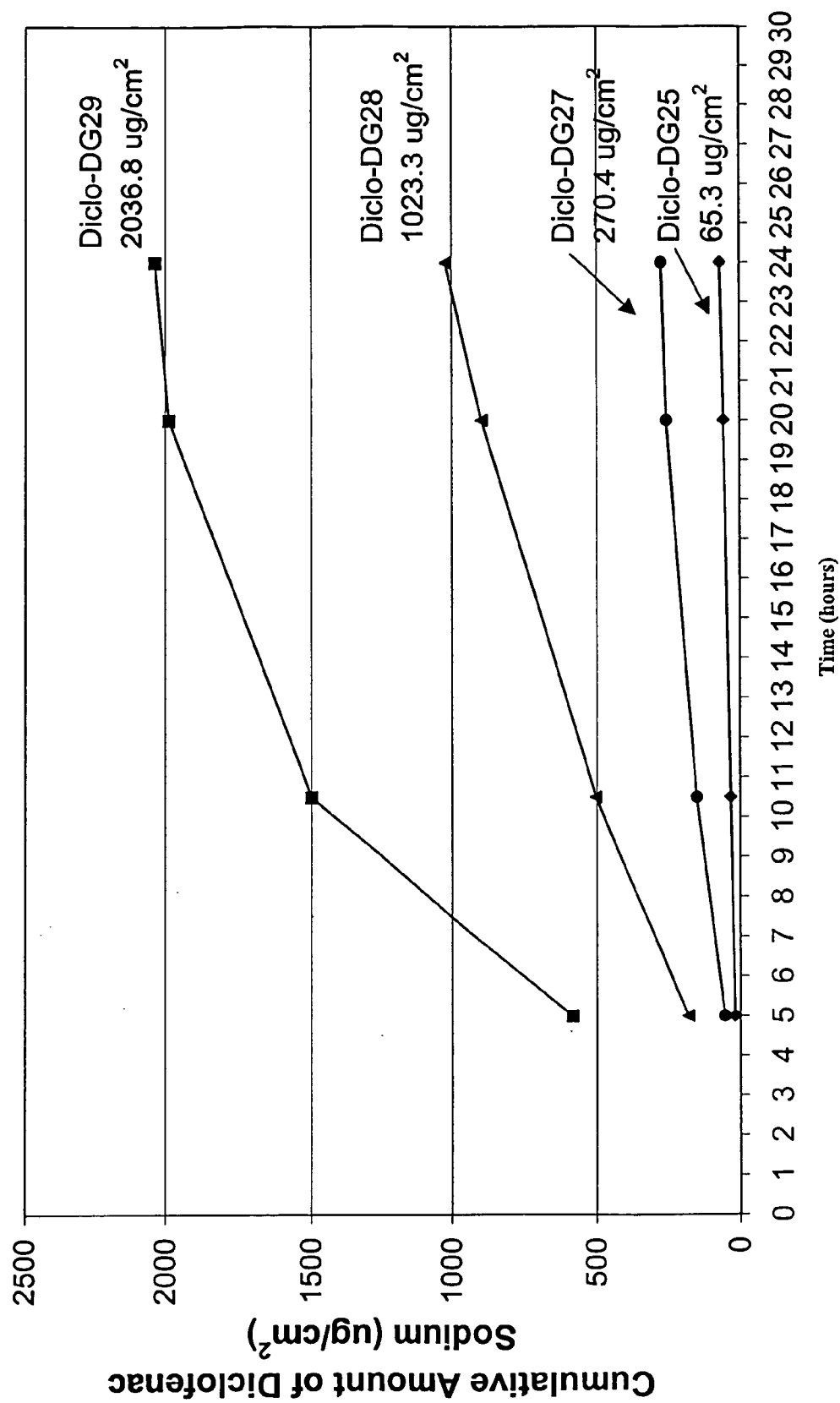
FIG. 4 is a graph illustrating the cumulative amount of diclofenac from a gel described in Example 5.

10% ethanol/90% water solution was used as the receiver solution. The volume of receiver solution was 8 ml. The receiver solution was collected and replaced with fresh ethanol/water solution at each time point. The receiver solution collected was analyzed by an HPLC for the concentration of diclofenac sodium. The cumulative amount of diclofenac sodium across human cadaver skin was calculated using the measured diclofenac sodium concentrations in the receiver solutions, which are shown in Table 14 and FIG. 4.

Since diclofenac sodium is not expected to react with NaOH, the NaOH concentration listed in Table 13 equals the excess NaOH concentration.

TABLE 13

Weight and Weight Percent of Each Component (Based on Total Solution Weight) for Four Diclofenac Sodium Transdermal Gels

|  | Diclo-DG25 | Diclo-DG27 | Diclo-DG28 | Diclo-DG29 |
|---|---|---|---|---|
| Diclofenac sodium | 0.3 g (14.1%) | 0.3 g (13.8%) | 0.3 g (13.7%) | 0.3 g (13.50%) |
| Propylene glycol | 0.6 g (28.2%) | 0.6 g (27.6%) | 0.6 g (27.4%) | 0.6 g (26.9%) |
| Ethyl alcohol | 1 g (46.9%) | 1 g (46.1%) | 1 g (45.7%) | 1 g (44.8%) |
| DI water | 0.2 g (9.4%) | 0.22 g (10.1%) | 0.23 g (10.5%) | 0.25 g (11.2%) |
| HPMC | 0.03 g (1.4%) | 0.03 g (1.4%) | 00.3 g (1.4%) | 0.03 g (1.3%) |
| NaOH | 0 | 0.02 g (0.9%) | 0.03 g (1.4%) | 0.05 g (2.2%) |

TABLE 14

Cumulative Amount of PPA-HCl across human cadaver skin for Diclofenac Sodium Transdermal Gels ($\mu g/cm^2$)

|  | Diclo-DG25 | Diclo-DG27 | Diclo-DG28 | Diclo-DG29 |
|---|---|---|---|---|
| 5 hours | 16.8 | 50.6 | 175.9 | 585.2 |
| 10.5 hours | 29.8 | 147.5 | 503.5 | 1499.8 |
| 20 hours | 53.4 | 252.3 | 896.4 | 1988.1 |
| 24 hours | 65.3 | 270.4 | 1023.3 | 2036.8 |

TABLE 15

Excess NaOH Concentration of Four Diclofenac Sodium Transdermal Gels

|  | Diclo-DG25 | Diclo-DG27 | Diclo-DG28 | Diclo-DG29 |
|---|---|---|---|---|
| Excess NaOH Concentration (wt %) | 0 | 0.9 | 1.4 | 2.2 |

The cumulative amount of diclofenac sodium across human cadaver skin at 24 hours increased from 65.3 μg/cm$^2$ to 2036.8 μg/cm$^2$ when the calculated excess NaOH concentration in the gel was increased from 0% to 2.2% (Table 15). The cumulative amount of diclofenac sodium across human cadaver skin at 24 hours from the gel containing 0.9% NaOH (Diclo-DG27) was 270.4 μg/cm$^2$, which was about 4 times higher than that from the formulation without NaOH (65.3 μg/cm$^2$, #Diclo-DG25).

EXAMPLE 6

An in-vitro skin permeation study was conducted using four diclofenac sodium transdermal systems. The formulations used to prepare these systems are listed in Table 16, which include weight and weight percent of each ingredient in the formulations. The weight of sodium hydroxide (NaOH) was 0 g, 0.01 g, 0.02 g, and 0.05 g for formulation #Diclo-P64, -P86, -P65, and -P87 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $^{11}/_{16}$ inch. The theoretical percent weight for each ingredient after drying (calculated assuming all the volatile ingredients were completely removed during drying) is listed in Table 17.

The in-vitro permeation of diclofenac sodium through human cadaver skin from these discs was performed using Franz-type diffusion cells with a diffusion area of 1 cm$^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Twelve diffusion cells were used for each formulation.

The cells were filled with 10% ethanol/90% water solution. At each time point, the pH at the interface between skin and the patch for three diffusion cells was measured by removing the receiving fluid, removing the clamp and the donor chamber, gently teasing the patch away from the skin with tweezers, leaving the skin on the receiver chamber, measuring the pH of the solution on the skin by placing the microelectrode directly onto the skin surface. The measured pHs at the skin/patch interface were listed in Table 18. For all other cells, the receiving fluid was completely withdrawn and replaced with fresh ethanol/water solution. The samples taken were analyzed by an HPLC for the concentration of diclofenac sodium in the receiver solution. The pHs of the receiver solutions taken were measured by a pH meter. The cumulative amount of diclofenac sodium across human cadaver skin was calculated using the measured diclofenac sodium concentrations in the receiver solutions, which were shown in Table 19. The pHs of the receiver solutions were listed in Table 20.

Since diclofenac sodium is not expected to react with NaOH, the NaOH concentration listed in Table 2 equals the excess NaOH concentration.

The pH of the patch was determined using the following procedures. A 2.5 cm$^2$ circular patch was punched out. Ten ml of purified water was pipetted into a glass vial, and a stir bar was added, the liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter. The measured pHs for the diclofenac sodium transdermal systems are listed in Table 21.

TABLE 16

Weight and Weight Percent of Each Ingredient Based on Total Solution Weight for Four Diclofenac Sodium Transdermal Systems

|  | Diclo-P64 | Diclo-P86 | Diclo-P65 | Diclo-P87 |
|---|---|---|---|---|
| Diclofenac sodium | 0.6 g (9.2%) | 0.6 g (9.2%) | 0.9 g (9.2%) | 0.6 g (9.1%) |
| Propylene glycol | 0.9 g (13.8%) | 0.9 g (13.8%) | 0.9 g (13.8%) | 0.9 g (13.6%) |
| NaOH | 0 | 0.01 g (0.2%) | 0.02 g (0.3%) | 0.05 g (0.8%) |
| PIB adhesive (30% solid) | 4 g (61.5%) | 4 g (61.3%) | 4 g (61.2%) | 4 g (60.6%) |
| Heptane | 1 g (15.4%) | 1 g (15.3%) | 1 g (15.3%) | 1 g (15.2%) |
| DI water | 0 | 0.01 g (0.2%) | 0.02 g (0.3%) | 0.05 g (0.8%) |

TABLE 17

Weight and Theoretical Weight Percent of Each Ingredient in the Dried Film for Four Diclofenac Sodium Transdermal Systems

|  | Diclo-P64 | Diclo-P86 | Diclo-P65 | Diclo-P87 |
|---|---|---|---|---|
| Diclofenac sodium | 0.6 g (22.2%) | 0.6 g (22.1%) | 0.9 g (22.1%) | 0.6 g (21.8%) |
| Propylene glycol | 0.9 g (33.3%) | 0.9 g (33.2%) | 0.9 g (33.1%) | 0.9 g (32.7%) |
| NaOH | 0 | 0.01 g (0.4%) | 0.02 g (0.7%) | 0.05 g (1.8%) |
| PIB adhesive | 1.2 g (44.4%) | 1.2 g (44.3%) | 1.2 g (44.1%) | 1.2 g (43.6%) |

TABLE 18 pHs at the Interface between Skin and Patch at Various Time Points for Diclofenac Sodium Transdermal Systems

|  | Diclo-P64 | Diclo-P86 | Diclo-P65 | Diclo-P87 |
|---|---|---|---|---|
| 3 hours | * | 11.0 | * | 10.3 |
| 6 hours | * | 11.0 | 11.2 | 9.8 |
| 10 hours | 8.5 | 10.9 | 10.7 | 10.2 |
| 24 hours | * | 9.7 | 10.1 | 9.4 |

*Cannot be measured because there was not enough solution at the interface

TABLE 19

Cumulative Amount of Diclofenac Sodium across human cadaver skin for Diclofenac Sodium Transdermal Systems (g/cm$^2$)

|  | Diclo-P64 | Diclo-P86 | Diclo-P65 | Diclo-P87 |
|---|---|---|---|---|
| 3 hours | 7.5 | 1.5 | 33.4 | 257.7 |
| 6 hours | 39.6 | 18.3 | 269.3 | 793.3 |
| 10 hours | 63.2 | 49.3 | 654.4 | 1652.2 |
| 24 hours | 34.6 | 227.7 | 1733.8 | 3257.7 |

TABLE 20 pHs of Receiver Solutions at Various Time Points for Diclofenac Sodium Transdermal Systems

|  | Diclo-P64 | Diclo-P86 | Diclo-P65 | Diclo-P87 |
|---|---|---|---|---|
| 3 hours | 8.1 | 8.0 | 9.3 | 10.8 |
| 6 hours | 7.4 | 7.9 | 7.7 | 10.0 |
| 10 hours | 7.0 | 7.6 | 7.3 | 7.7 |
| 24 hours | 7.0 | 8.9 | 7.5 | 9.6 |

TABLE 21

Excess NaOH Concentration and pH of Four Diclofenac Sodium Transdermal Systems

|  | Diclo-P64 | Diclo-P86 | Diclo-P65 | Diclo-P87 |
|---|---|---|---|---|
| Excess NaOH Concentration (wt %) | 0 | 0.4 | 0.7 | 1.8 |
| pH | 7.40 | 8.99 | 10.71 | 10.38 |

The cumulative amount of diclofenac sodium across human cadaver skin at 24 hours increased from 34.6 g/cm$^2$ to 3257.7 g/cm$^2$ (Table 19) when the calculated excess NaOH concentration in the dried patch was increased from 0% to 1.8% (Table 17). The cumulative amount of diclofenac sodium across human cadaver skin at 24 hours from the system containing 0.4% NaOH (Diclo-P86) was 227.7 g/cm$^2$, which was about six times higher than that from the formulation without NaOH (34.6 g/cm2, #Diclo-P64). This result indicated that the permeation of diclofenac sodium across human skin could be enhanced by a NaOH concentration as low as 0.4%.

The pHs at the interface between skin and the patch were about the same as shown in Table 18, even though the concentration of NaOH was increased from 0.4% to 1.8%. It was noticed that the less the amount of solution at the interface, the higher the NaOH concentration. It was difficult to measure the pH of interface between skin and patch for the formulations without NaOH or with a low NaOH concentration because there was not enough solution on the top of the skin.

Since the pH measurement for the interface between skin and patch may be difficult for low NaOH concentrations, the pHs of the receiver solutions were measured at various time points. The pHs of receiver solutions listed in Table 20 indicated that the pHs depend on the time interval between sampling, the NaOH concentration in the patch, and the time point. The pHs at the 3-hour time point increased from 8 to 10.8 when the NaOH concentration in the patch was increased from 0.4% to 1.8%.

The pH of the diclofenac sodium patch measured using the procedures listed above increased from 7.40 to 10.38 when the calculated excess NaOH concentration in the dried patch was increased from 0% to 1.8% (Table 21).

We claim:

1. A composition of matter useful for the delivery of a nonsteroidal anti-inflammatory drug through a body surface, comprising a formulation comprising: (a) a therapeutically effective amount of a nonsteroidal anti-inflammatory drug; (b) a hydroxide-releasing agent in an amount effective to enhance the flux of the drug through the body surface without causing damage thereto and effective to provide a pH in the range of approximately 8.0 to 13 at the body surface, during drug administration; and wherein the amount of hydroxide-releasing agent in the formulation is the total of (a) the amount required to neutralize any acidic species in the formulation plus (b) an amount equal to approximately 0.5 to 25.0 wt % of the formulation; and (c) a pharmaceutically acceptable carrier suitable for topical or transdermal drug administration, wherein:

the composition is provided in a transdermal patch comprising a laminated structure that is to be affixed to the skin, the structure comprising a drug reservoir comprising the formulation contained within a polymeric matrix of a pharmaceutically acceptable adhesive material that serves to affix the system to the skin during drug delivery, and wherein the hydroxide-releasing agent comprises an inorganic hydroxide selected from the group consisting of sodium hydroxide and potassium hydroxide.

2. The composition of claim 1, wherein the pH at the body surface is in the range of approximately 8.0 to 11.5.

3. The composition of claim 2, wherein the pH at the body surface is in the range of approximately 8.5 to 11.5.

4. The composition of claim 1, wherein the carrier is aqueous.

5. The composition of claim 1, wherein the composition is free of additional permeation enhancers.

6. The composition of claim 1, wherein the composition is free of organic solvents.

7. The composition of claim 1, wherein the hydroxide-releasing agent releases free hydroxide ions in the presence of an aqueous fluid.

8. The composition of claim 1, wherein the amount of inorganic hydroxide in the formulation is the total of
 (a) the amount required to neutralize any acidic species in the formulation plus
 (b) an amount equal to approximately 0.5 wt % to 4.0 wt % of the formulation.

9. The composition of claim 1, wherein the drug is systemically acting.

10. The composition of claim 1, wherein the drug is a propionic acid derivative.

11. The composition of claim 10, wherein the propionic acid derivative is selected from the group consisting of ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, tiaprofenic acid, salts, esters, amides of any of the foregoing, and combinations thereof.

12. The composition of claim 11, wherein the propionic acid derivative is selected from the group consisting of ketoprofen and ibuprofen.

13. The composition of claim 1, wherein the drug is selected from the group consisting of acetylsalicylic acid, apazone, diclofenac, difenpiramide, diflunisal, etodolac, flufenamic acid, indomethacin, ketorolac, meclofenamate, mefenamic acid, nabumetone, phenylbutazone, piroxicam, salicylic acid, sulindac, tolmetin, salts, esters, amides of any of the foregoing, and combinations thereof.

14. The composition of claim 13, wherein the drug is selected from the group consisting of diclofenac, ketorolac, and piroxicam.

15. A system for the topical or transdermal administration of a nonsteroidal anti inflammatory drug, comprising: (a) at least one drug reservoir containing the drug and a hydroxide-releasing agent in an amount effective to enhance the flux of the drug through the body surface without causing damage thereto and effective to provide a pH in the range of approximately 8.0 to 13 at the body surface during drug administration; and wherein the amount of hydroxide-releasing agent in the reservoir is the total of (a) the amount required to neutralize any acidic species in the reservoir plus (b) an amount equal to approximately 0.5 to 25.0 wt % of the reservoir; (b) a means for maintaining the system in drug and enhancer transmitting relationship to the body surface; and (c) a backing layer that serves as the outer surface of the system during use, wherein the drug reservoir is comprised of a polymeric adhesive, wherein the hydroxide-releasing agent comprises an inorganic hydroxide selected from the group consisting of sodium hydroxide and potassium hydroxide.

16. The system of claim 15, wherein the pH at the body surface is in the range of approximately 8.0 to 11.5.

17. The system of claim 16, wherein the pH at the body surface is in the range of approximately 8.5 to 11.5.

18. The system of claim 15, wherein the backing layer is occlusive.

19. The system of claim 15, wherein the polymeric adhesive serves as the means for maintaining the system in drug and enhancer transmitting relationship to the body service.

20. The system of claim 15, wherein the drug is systemically acting.

21. The system of claim 15, wherein the drug is a propionic acid derivative.

22. The system of claim 21, wherein the propionic acid derivative is selected from the group consisting of ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, tiaprofenic acid, salts, esters, amides of any of the foregoing, and combinations thereof.

23. The system of claim 22, wherein the propionic acid derivative is selected from the group consisting of ketoprofen and ibuprofen.

24. The system of claim 15, wherein the drug is selected from the group consisting of acetylsalicylic acid, apazone, diclofenac, difenpiramide, diflunisal, etodolac, flufenamic acid, indomethacin, ketorolac, meclofenamate, mefenamic acid, nabumetone, phenylbutazone, piroxicam, salicylic acid, sulindac, tolmetin, salts, esters, amides of any of the foregoing, and combinations thereof.

25. The system of claim 24, wherein the drug is selected from the group consisting of diclofenac, ketorolac, and piroxicam.

26. A composition according to claim 1 wherein the adhesive comprises a pressure-sensitive adhesive (PSA) that is suitable for long-term skin contact, and that is physically and chemically compatible with the active agent and hydroxide-releasing agent.

27. A composition according to claim 26 wherein the adhesive comprises polyisobutylene.

28. A composition according to claim 26 wherein the patch is adapted to deliver the drug through a defined area of intact unbroken living skin or mucosal tissue having an area of about 20 $cm^2$ to about 60 $cm^2$.

29. A composition according to claim 26 wherein the flux of the active agent through the body surface is increased relative to the rate that would be obtained in the absence of permeation enhancement, and the nonsteroidal anti-inflammatory drug permeates through the body surface of a patient, without causing damage thereto.

30. A composition according to claim 29 wherein the hydroxide-releasing agent represents about 0.5 wt % to 3.0 wt % of the formulation, and the concentration of the active agent in the formulation is between about 5 wt % to 20 wt % of the weight of the polymeric matrix.

31. A composition according to claim 30 wherein the patch further comprises a flexible elastomeric backing layer that functions as the primary structural element of the transdermal system and provides the device with flexibility and occlusivity, the backing layer being inert and incapable of absorbing drug, hydroxide-releasing agent, or components of the formulation contained within the device, and that permits the device to follow the contours of the skin and be worn comfortably on areas of skin such as at joints or other points of flexure.

32. A composition according to claim 31 wherein the backing layer is formed from a synthetic polymer selected from the group consisting of polyester, polyethylene, polypropylene, polyurethane, polyvinylidine chloride, polyether amide, natural polymers, and macroporous woven and nonwoven materials.

33. A composition according to claim 1 wherein the adhesive material comprises polyisobutylene.

34. A composition according to claim 1 wherein the patch is adapted to deliver the drug through a defined area of intact unbroken living skin or mucosal tissue having an area of about 20 $cm^2$ to about 60 $cm^2$.

35. A composition according to claim 1 wherein the flux of the active agent through the body surface is increased relative to the rate that would be obtained in the absence of permeation enhancement, and the nonsteroidal anti-inflammatory drug permeates through the body surface of a patient, without causing damage thereto.

36. A composition according to claim 1 wherein the hydroxide-releasing agent represents about 0.5 wt % to 3.0 wt % of the formulation, and the concentration of the active agent in the formulation is between about 5 wt % to 20 wt % of the weight of the polymeric matrix.

37. A composition according to claim 1 wherein the patch further comprises a flexible elastomeric backing layer.

38. A composition according to claim 37 wherein the backing layer is formed from a synthetic polymer selected from the group consisting of polyester, polyethylene, polypropylene, polyurethane, polyvinylidine chloride, polyether amide, natural polymers, and macroporous woven and nonwoven materials.

39. A system according to claim 15 wherein the polymeric adhesive comprises polyisobutylene.

40. A system according to claim 15 wherein the patch is adapted to deliver the drug through a defined area of intact unbroken living skin or mucosal tissue having an area of about 20 $cm^2$ to about 60 $cm^2$.

41. A system according to claim 15 wherein the flux of the active agent through the body surface is increased relative to the rate that would be obtained in the absence of permeation enhancement, and the nonsteroidal anti-inflammatory drug permeates through the body surface of a patient, without causing damage thereto.

42. A system according to claim 15 wherein the hydroxide-releasing agent represents about 0.5 wt % to 3.0 wt % of the formulation, and the concentration of the active agent in the formulation is between about 5 wt % to 20 wt % of the weight of the polymeric matrix.

43. A system according to claim 15 wherein the patch further comprises a flexible elastomeric backing layer that functions as the primary structural element of the transdermal system and provides the device with flexibility and occlusivity, the backing layer being inert and incapable of absorbing drug, hydroxide-releasing agent, or components of the formulation contained within the device, and that permits the device to follow the contours of the skin and be worn comfortably on areas of skin such as at joints or other points of flexure.

44. A system according to claim 15 wherein the backing layer is formed from a synthetic polymer selected from the group consisting of polyester, polyethylene, polypropylene, polyurethane, polyvinylidine chloride, and polyether amide, natural polymers, and macroporous woven and nonwoven materials.

\* \* \* \* \*